(12) United States Patent
Takahashi

(10) Patent No.: US 10,736,488 B2
(45) Date of Patent: *Aug. 11, 2020

(54) FLEXIBLE TUBE INSERTION APPARATUS COMPRISING VARIABLE STIFFNESS INSERTION SECTION TO BE INSERTED INTO SUBJECT

(71) Applicant: OLYMPUS CORPORATION, Tokyo (JP)

(72) Inventor: Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

This patent is subject to a terminal disclaimer.

(21) Appl. No.: 15/825,286

(22) Filed: Nov. 29, 2017

(65) Prior Publication Data

US 2018/0078118 A1 Mar. 22, 2018

Related U.S. Application Data

(63) Continuation of application No. PCT/JP2015/066215, filed on Jun. 4, 2015.

(51) Int. Cl.
*A61B 1/00* (2006.01)
*A61B 1/04* (2006.01)
*A61B 1/31* (2006.01)

(52) U.S. Cl.
CPC ...... *A61B 1/00071* (2013.01); *A61B 1/00006* (2013.01); *A61B 1/00009* (2013.01);
(Continued)

(58) Field of Classification Search
CPC ............ A61B 1/00071; A61B 1/00078; A61B 1/00006; A61B 1/00009; A61B 1/00133;
(Continued)

(56) References Cited

U.S. PATENT DOCUMENTS 4,054,128 A * 10/1977 Seufert ............... A61B 1/00082
600/116
5,018,509 A * 5/1991 Suzuki ................. A61B 1/0005
348/65

(Continued)

FOREIGN PATENT DOCUMENTS

JP S6137931 B2 8/1986
JP H06181882 A 7/1994
(Continued)

OTHER PUBLICATIONS

Japanese Office Action dated Sep. 18, 2018 in Japanese Patent Application No. 2017-521451.
(Continued)

*Primary Examiner* — John P Leubecker
(74) *Attorney, Agent, or Firm* — Scully, Scott, Murphy & Presser, P.C.

(57) ABSTRACT

A flexible tube insertion apparatus includes an insertion section including a bending portion and a flexible tube portion, variable stiffness sections which causes a change in a level of a bending stiffness of the flexible tube portion, a variable stiffness control section which controls the change in the bending stiffness of the flexible tube portion by the variable stiffness sections, an image sensor which images a subject in a forward direction of the bending portion, a cavity detection section which detects a presence of a cavity in the forward direction based on an image from the image sensor, and a time setting section that sets a time period. The bending stiffness is switched each time period set by the time setting section when the cavity detection section has detected the presence of the cavity in the forward direction.

7 Claims, 16 Drawing Sheets

(52) U.S. Cl.
CPC ...... *A61B 1/00078* (2013.01); *A61B 1/00163* (2013.01); *A61B 1/04* (2013.01); *A61B 1/31* (2013.01); *A61B 1/00114* (2013.01); *G06T 2207/30028* (2013.01)

(58) Field of Classification Search
CPC ........... A61B 1/0051; A61B 1/01; A61B 1/31; G06T 2207/30028
See application file for complete search history.

(56) References Cited

U.S. PATENT DOCUMENTS

| 2006/0015011 | A1 | 1/2006 | Hasegawa et al. | |
| 2007/0038028 | A1* | 2/2007 | Uchimura | A61B 1/00071 600/144 |
| 2007/0149852 | A1* | 6/2007 | Noguchi | A61B 1/00082 600/144 |
| 2011/0065993 | A1* | 3/2011 | Belson | A61B 1/0053 600/141 |
| 2011/0160534 | A1* | 6/2011 | Lee | A61B 1/00009 600/109 |
| 2011/0319714 | A1* | 12/2011 | Roelle | A61B 1/00006 600/118 |
| 2012/0008860 | A1* | 1/2012 | Hirota | G06T 7/0012 382/165 |
| 2015/0025316 | A1 | 1/2015 | Hasegawa et al. | |
| 2015/0092993 | A1* | 4/2015 | Kanda | A61B 1/00009 382/106 |
| 2018/0064310 | A1 | 3/2018 | Takahashi et al. | |
| 2018/0296281 | A1* | 10/2018 | Yeung | A61B 34/30 |

FOREIGN PATENT DOCUMENTS

| JP | 2004167010 A | 6/2004 |
| JP | 5676058 B1 | 2/2015 |
| WO | 2016/181484 A1 | 11/2016 |

OTHER PUBLICATIONS

International Search Report dated Sep. 1, 2015 issued in PCT/JP2015/066215.
English translation of International Preliminary Report on Patentability dated Dec. 14, 2017 together with the Written Opinion in related International Application No. PCT/JP2015/066215.

* cited by examiner

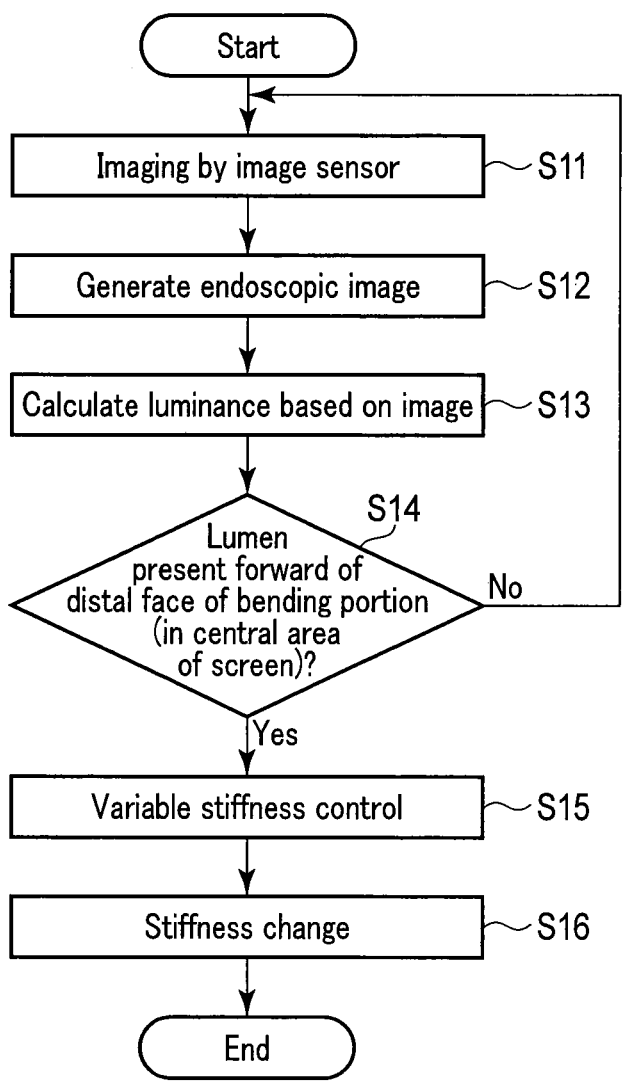
F I G. 10

Lumen detection area D in forward direction

Lumen detection area D in forward direction

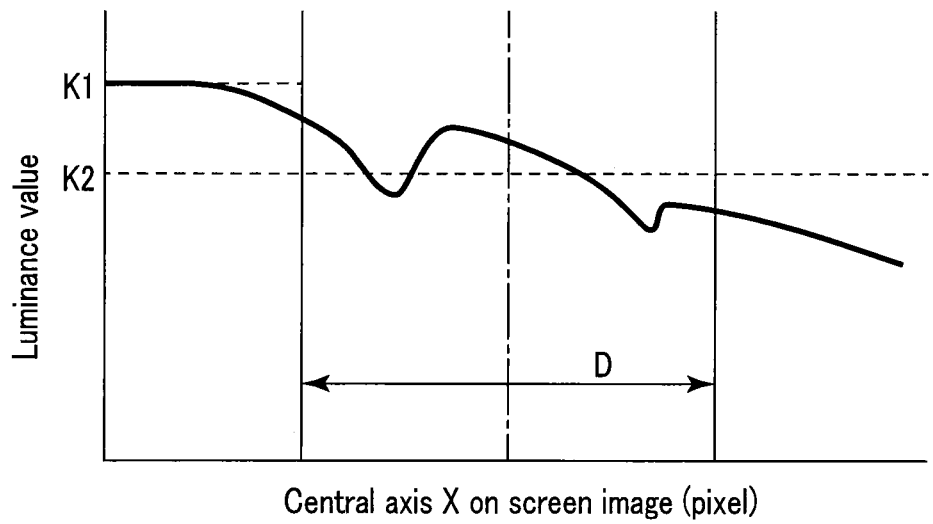
F I G. 13
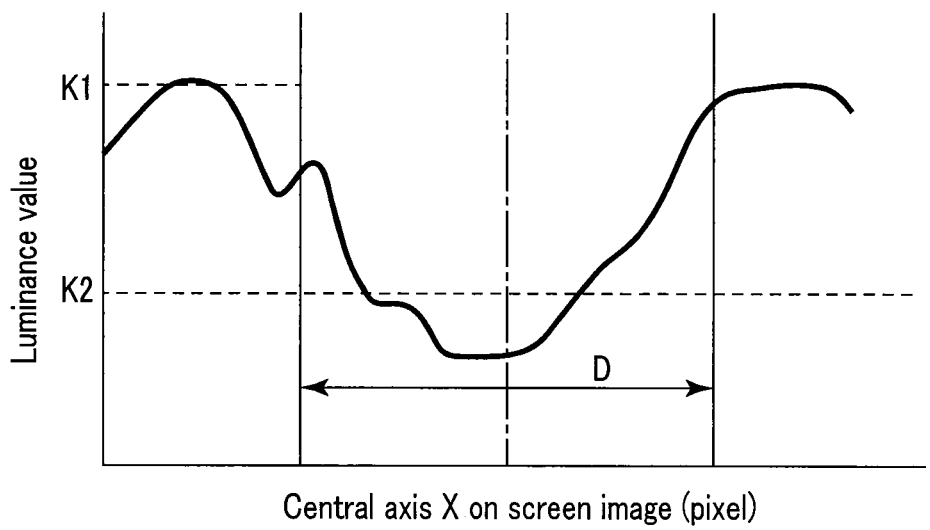
F I G. 14

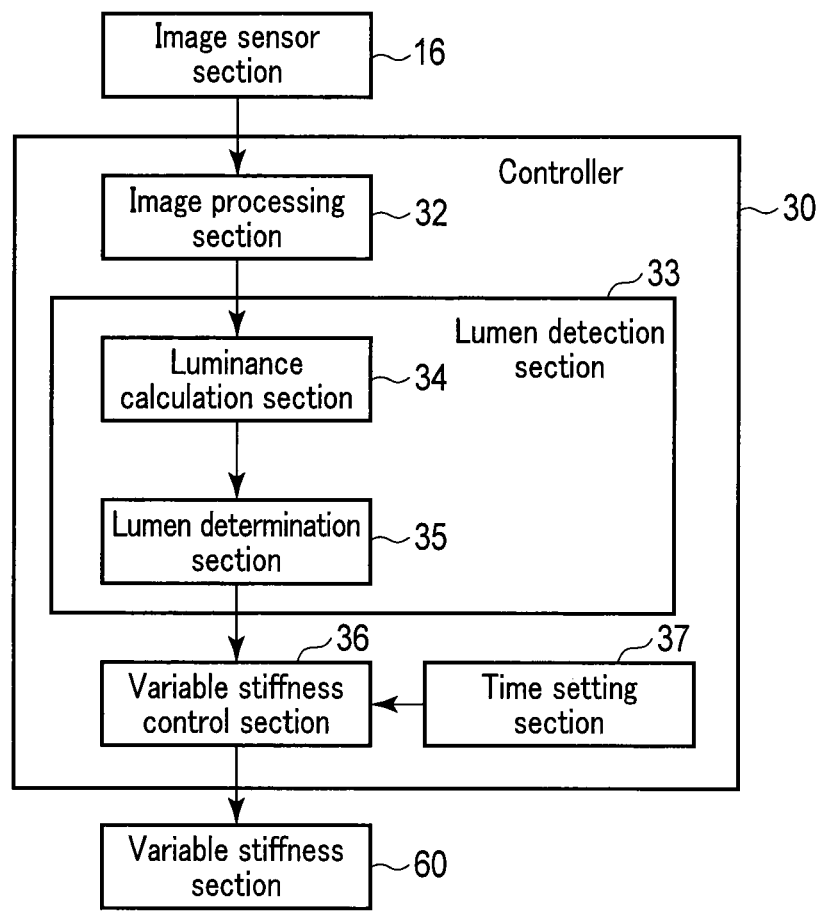
F I G. 20

FLEXIBLE TUBE INSERTION APPARATUS COMPRISING VARIABLE STIFFNESS INSERTION SECTION TO BE INSERTED INTO SUBJECT

CROSS-REFERENCE TO RELATED APPLICATIONS

This application is a Continuation Application of PCT Application No. PCT/JP2015/066215, filed Jun. 4, 2015, the entire contents of all of which are incorporated herein by references.

BACKGROUND OF THE INVENTION

1. Field of the Invention

The present invention relates to a flexible tube insertion apparatus comprising an insertion section to be inserted into a subject.

2. Description of the Related Art

The large intestine roughly consists of the rectum, the colon, and the cecum from the side of the anus. The colon further consists of the sigmoid colon, the descending colon, the transverse colon, and the ascending colon from the rectum side. Normally, the sigmoid colon and the transverse colon are not fixed in the abdomen, and have freedom of movement. When a flexible, elongated insertion section of a flexible tube insertion apparatus (e.g., an endoscope apparatus) is inserted into such an intestinal tract, the insertion section bends along the intestinal wall while passing through the intestinal tract. However, as the insertion section is further advanced from the hand side, the flexible insertion section may be bent in a direction different from the direction in which the force is applied in the intestine, preventing the distal end of the insertion section from passing smoothly. To address such a problem, a technique for facilitating transmission of a force to the direction in which the insertion section should desirably be inserted by increasing the bending stiffness of the insertion section is known. This is implemented either by increasing the bending stiffness of the insertion section itself, or by attaching a member different from the insertion section, such as an overtube (sliding tube), to the insertion section.

However, when the bending stiffness of the entire insertion section is uniformly changed, the stiffness cannot be changed according to the bending state of the insertion section inside the intestinal tract. Accordingly, the insertion section may be stuck in, for example, the sigmoid colon and excessively extend the sigmoid colon, causing distress to the patient. Such an insertion section is inconvenient for insertion into a deep portion.

Jpn. Pat. Appln. KOKOKU Publication No. 61-37931 discloses an endoscope comprising an insertion section including an elongated, flexible tube portion divided into a plurality of areas in the longitudinal direction to cause the areas to have different levels of flexibility. In the endoscope, having different levels of flexibility at the areas of the flexible tube portion allows distress at a patient during insertion to be reduced, thus the ease of insertion is improved.

BRIEF SUMMARY OF THE INVENTION

According to one embodiment of the present invention, a flexible tube insertion apparatus is provided. The flexible tube insertion apparatus comprises a tubular insertion section to be inserted into a subject and including a bending portion located distally on the insertion section, and a flexible tube portion located proximal to the bending portion, a plurality of variable stiffness sections each provided in a corresponding one of a plurality of segments defined in a longitudinal axis direction of the flexible tube portion and configured to cause a change in a level of a bending stiffness of the flexible tube portion on a segment-by-segment basis, a variable stiffness control section that controls the change in the bending stiffness of the flexible tube portion by the variable stiffness sections, an image sensor that is provided in the bending portion and images a forward direction of the bending portion, a cavity detection section that detects a presence of a cavity in the forward direction of the bending portion, based on an image acquired by the imaging by the image sensor, and a time setting section that sets a time period at which the bending stiffness is changed by the variable stiffness sections. The variable stiffness control section controls the changes in the bending stiffness of the variable stiffness sections in such a manner that the relationship of levels between the bending stiffness of adjacent variable stiffness sections is switched at the time period set by the time setting section when the cavity detection section has detected the presence of the cavity in an approximately forward direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 10 is a flowchart illustrating variable stiffness control according to the first embodiment.

FIG. 13 is a graph showing an example of a relationship between a central axis X on a screen image (pixel) and a luminance value in the endoscopic image shown in FIG. 11.

FIG. 14 is a graph showing an example of a relationship between the central axis X on the screen image (pixel) and the luminance value in the endoscopic image shown in FIG. 12.

FIG. 20 is a block diagram illustrating variable stiffness control according to a third embodiment.

DETAILED DESCRIPTION OF THE INVENTION

First Embodiment

The first embodiment of the present invention will be described with reference to FIGS. 1 to 15.

Figure 1:
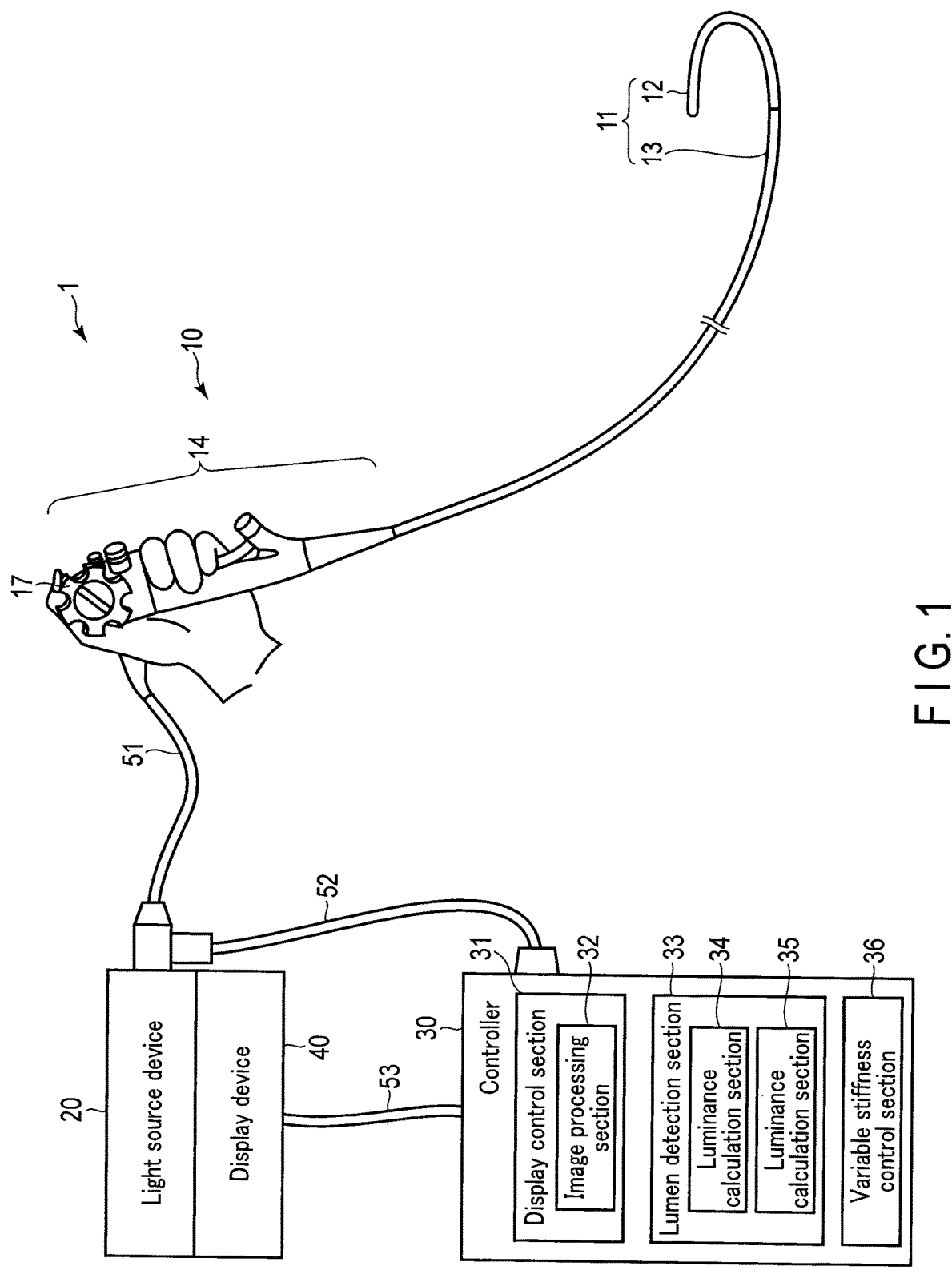
FIG. 1 is a diagram schematically showing a configuration of an endoscope apparatus according to a first embodiment.

FIG. 1 is a diagram schematically showing a configuration of an endoscope apparatus 1, which is a flexible tube insertion apparatus. The endoscope apparatus 1 comprises an endoscope 10, a light source device 20, a controller 30, and a display device 40.

The endoscope 10 includes a tubular insertion section 11 to be inserted into a subject, and an operation section 14 located proximal to the insertion section 11. The endoscope 10 is, for example, a colonoscope. That is, the subject is the large intestine (intestinal tract).

Figure 2:
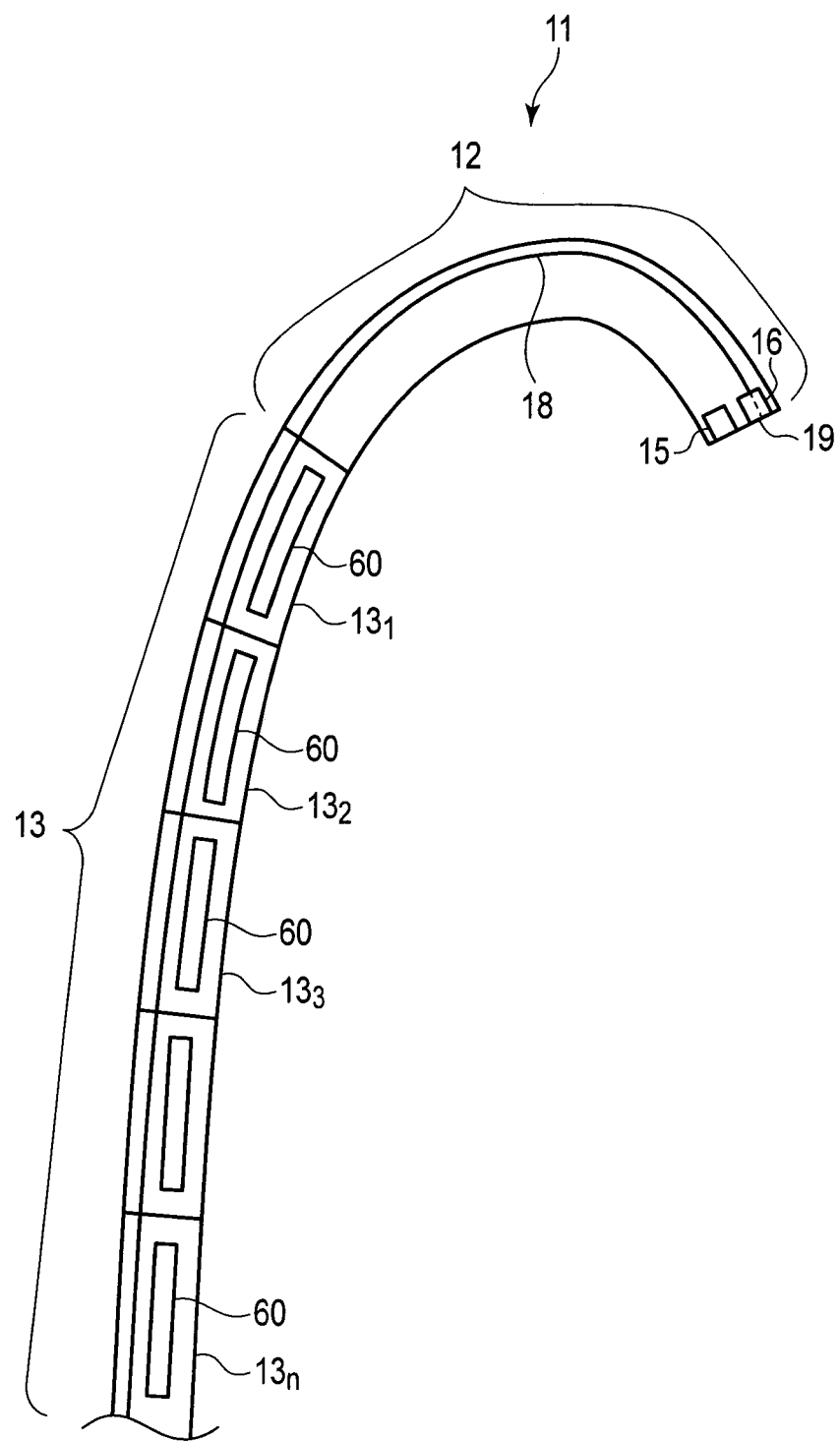
FIG. 2 is an enlarged view schematically showing a bending portion and a flexible tube portion.

The insertion section 11 includes a bending portion 12 located distally on the insertion section 11 and a flexible tube portion 13 located proximal to the bending portion 12. As shown in FIG. 2, the bending portion 12 incorporates, for example, an illumination section 15 and an image sensor section 16 that images a subject. The image sensor section 16 includes an observation optical system (not shown in FIG. 2) and an image sensor, e.g., a Charge Coupled Device (CCD). In the present embodiment, they are arranged along the longitudinal direction (axial direction) on the insertion section 11 (forward-viewing endoscope). The flexible tube portion 13 is an elongated tube that is bendable and flexible.

The operation section 14 is the portion of the endoscope 10 that is gripped by the user, as shown in FIG. 1. The operation section 14 includes an angle knob 17, which is a bending operation section. The angle knob 17 is coupled to the bending portion 12 via an angle wire 18 (not shown in FIG. 1), which has at least one pulling member inserted through the insertion section 11 in its longitudinal direction. FIG. 2 shows the angle wire 18 extending from the bending portion 12 to the flexible tube portion 13 inside the insertion section 11 along its inner surface. A distal end of the angle wire 18 is fixed to the bending portion 12. When the user rotates the angle knob 17, the angle wire 18 coupled thereto is moved, causing the bending portion 12 to be bent in a desired direction.

FIG. 2 is an enlarged view schematically showing the bending portion 12 and the flexible tube portion 13. For convenience, let us assume that the flexible tube portion 13 comprises a plurality of continuous segments (virtual units into which the flexible tube portion 13 is evenly divided as viewed in the longitudinal direction) defined in the longitudinal axis direction thereof. In FIG. 2, segments $13_1$, $13_2$, $13_3$, . . . , and $13_n$ of the flexible tube portion 13 are shown. A variable stiffness section 60 is provided in each of the segments. The variable stiffness section 60 is a variable stiffness actuator that allows to change the bending stiffness of the flexible tube portion 13 on a segment-by-segment basis.

Referring back to FIG. 1, the endoscope 10 is connected to the light source device 20 via a universal cord 51 extending proximally from the operation section 14. The universal cord 51 includes a light guide (optical fiber) connected to the illumination section 15, an electric cable connected to the image sensor section 16, a variable stiffness section control signal cable, etc. The light source device 20 supplies light to be emitted from the illumination window of the illumination section 15 on a distal face 19 of the bending portion 12 via the light guide.

The controller 30 is formed of a device including a CPU and the like. The controller 30 includes a display control section 31 including an image processing section 32, a lumen detection section 33 including a luminance calculation section 34 and a lumen determination section 35, and a variable stiffness control section 36. The display control section 31 is connected to the electric cable in the universal cord 51 via a cable 52, and thereby connected to the endoscope 10 (the image sensor section 16 in the bending portion 12). The display control section 31 is also connected to the display device 40 via a cable 53. The variable stiffness control section 36 is connected to the variable stiffness section 60 via the cable 52 and the variable stiffness section control signal cable included in the universal cord 51.

Figure 3:
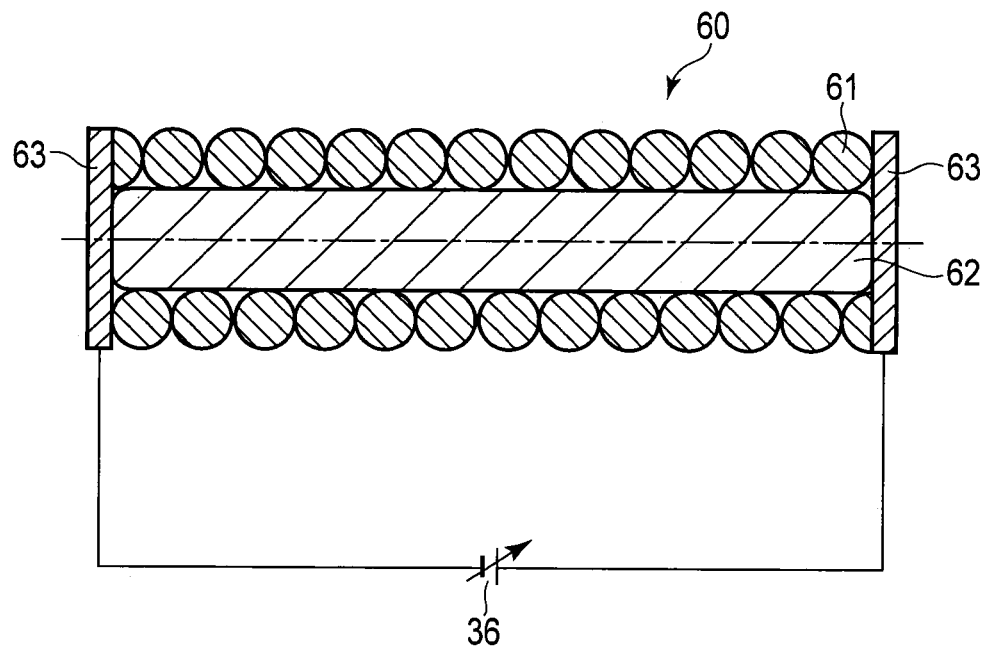
FIG. 3 is a diagram schematically showing an example of a configuration of a variable stiffness section.

FIG. 3 is a diagram schematically showing an example of a configuration of the variable stiffness section 60. The variable stiffness section 60 includes a coil pipe 61 formed of a metal wire, an electroactive polymer artificial muscle (EPAM) 62 encapsulated in the coil pipe 61, and electrodes 63 provided on both ends of the coil pipe 61. The variable stiffness section 60 is connected to the variable stiffness control section 36, and thus a voltage may be applied from the variable stiffness control section 36 to the EPAM 62 in the coil pipe 61 via the electrodes 63. The EPAM 62 is an actuator that changes its stiffness by extending and contracting according to an applied voltage. The variable stiffness section 60 is incorporated into the flexible tube portion 13 in such a manner that the central axis of the coil pipe 61 coincides with or is parallel to the central axis of the flexible tube portion 13.

Figure 4:
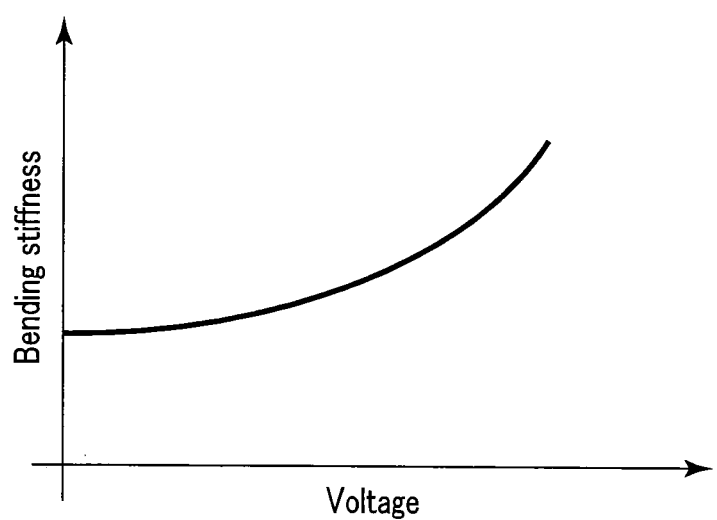
FIG. 4 is a diagram showing a voltage-bending stiffness characteristic of the variable stiffness section.

An electrode 63 (the EPAM 62) of the variable stiffness section 60 is applied with a voltage, which is a variable stiffness section control signal, from the variable stiffness control section 36 via the cable 52 and an electric cable in the universal cord 51. When such a voltage is applied, the EPAM 62 tends to extend its diameter with the central axis of the coil pipe 61 at its center. However, the EPAM 62 is surrounded by the coil pipe 61, and is restrained from extending its diameter. Accordingly, the bending stiffness of the variable stiffness section 60 increases as the value of the applied voltage increases, as shown in FIG. 4. That is, when the variable stiffness control section 36 changes the voltage applied to the variable stiffness section 60, the stiffness of the variable stiffness section 60 changes, and the bending stiffness of the flexible tube portion 13 incorporating the variable stiffness section 60 also changes.

The above-described configuration of the variable stiffness section 60 is merely an example. The variable stiffness section 60 is not limited to the one that allows the bending stiffness to be changed in response to a variable stiffness section control signal from the variable stiffness control section 36.

Next, the operation of the endoscope apparatus 1, which is colonoscopy in this case, will be described.

Let us assume that, at the start of insertion, the flexible tube portion 13 has a predetermined bending stiffness value that is neither the minimum bending stiffness value nor the maximum bending stiffness value of the variable stiffness section 60. That is, each segment of the flexible tube portion 13 may be stiffened or softened, compared to the state at the start of insertion, by causing the bending stiffness of the variable stiffness section 60 to change in response to the variable stiffness section control signal from the variable stiffness control section 36.

The insertion section 11 of the endoscope 10 is inserted by the user into an intestinal tract, which is a subject to be examined (from the anus through the rectum into the colon). The insertion section 11 passes through the intestinal tract while bending to follow the shape inside of the intestinal tract. An optical image of the observation target acquired by an observation optical system on a distal face of the bending portion 12 is converted into an electric signal by the image sensor section 16. The electric signal is output to the display control section 31 of the controller 30. The display control section 31 causes the image processing section 32 to generate an image signal of the observation target on the basis of the output electric signal. The display control section 31 then causes the display device 40 to display an image of an inside of an intestinal tract, that is, endoscopic image, on the basis of the generated image signal. The user advances the insertion section 11 while checking the lumen direction in the endoscopic image.

Figure 5:
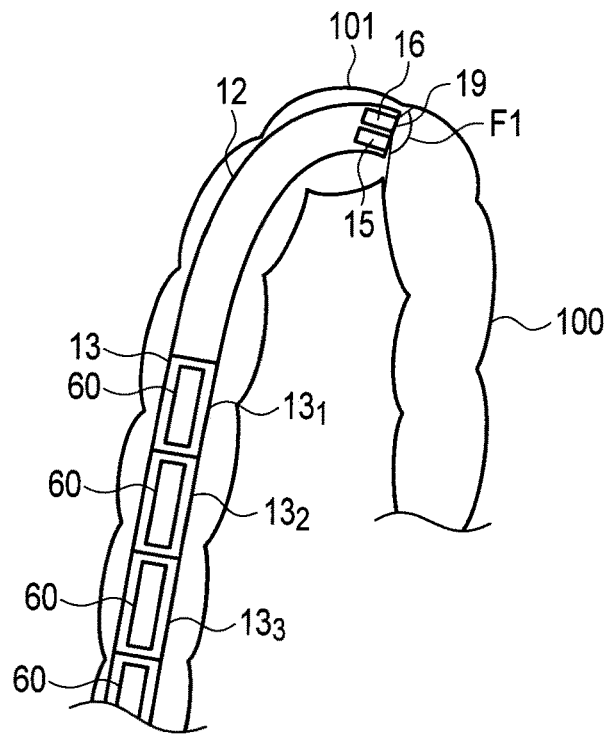
FIG. 5 is a diagram schematically showing an example of a state in which a distal face of the bending portion faces the intestinal wall while an insertion section is inserted into the large intestine in the first embodiment.
Figure 6:
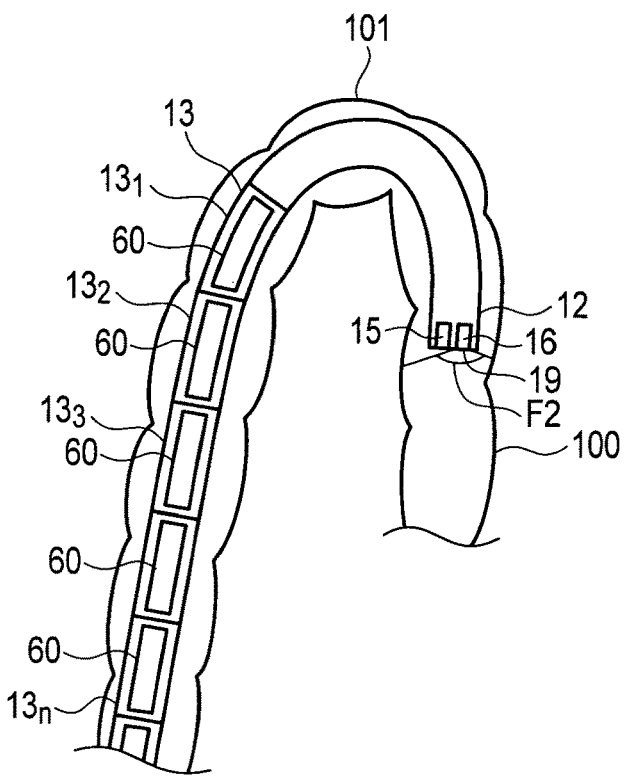
FIG. 6 is a diagram schematically showing an example of a state in which the distal face of the bending portion faces a lumen while an insertion section is inserted into the large intestine in the first embodiment.
Figure 7:
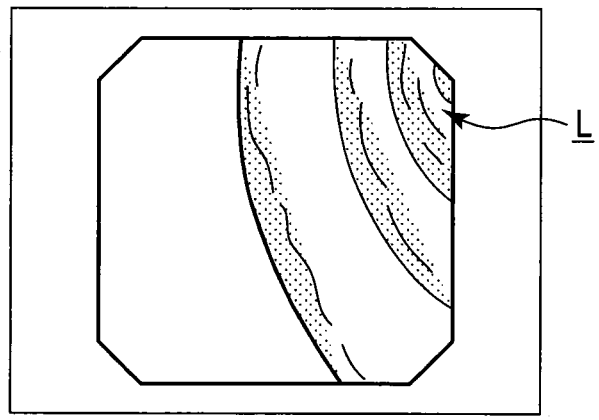
FIG. 7 shows an example of an image acquired by the endoscope apparatus in the state shown in FIG. 5.

FIGS. 5 and 6 schematically show an example of the insertion section 11 inserted into the large intestine. At first, the bending portion 12 located distally on the insertion section 11 is in a substantially straight state and passes through a substantially straight area inside an intestinal tract 100. When the bending portion 12 reaches a flexure 101 (e.g., the sigmoid colon) in the intestinal tract 100, the bending portion 12 passes while bending to follow the shape of the curvature of the flexure 101 in response to a user's operation of the angle knob 17, as shown in FIG. 5. In the state shown in FIG. 5, the distal face 19 of the bending portion 12 faces the intestinal wall. In other words, a lumen L (see FIG. 7) is not located at the center of the distal face 19 in the forward direction, that is, the center of the endoscopic field of view F1. Accordingly, a lumen L is not captured in the central region of the image (endoscopic image) acquired by the endoscope apparatus 1 in the state shown in FIG. 5, and a lumen L is captured outside the central region, as shown in FIG. 7. Accordingly, the lumen L locates out of the central region, the intestinal wall located in the forward direction of the distal face 19 is captured in the central region of the image.

Figure 8:
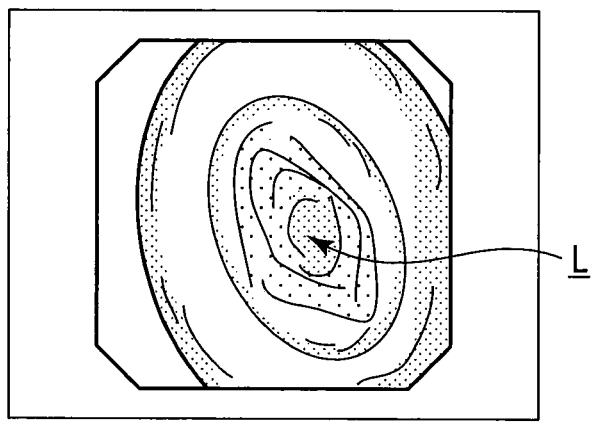
FIG. 8 shows an example of an image acquired by the endoscope apparatus in the state shown in FIG. 6.

When the bending portion 12 further advances in the intestinal tract 100, the flexible tube portion 13 comes close to the flexure 101, as shown in FIG. 6. At this time, the distal portion of the bending portion 12 has already passed through the flexure 101, and the distal face 19 of the bending portion 12 faces a lumen L (see FIG. 8) in response to a user's operation of the angle knob 17. In other words, the lumen L is located at the center in the forward direction of the distal face 19, that is, the center of the endoscopic field of view F2, and the distal face 19 is approximately orthogonal to the direction along the lumen L. Accordingly, the lumen L is captured at the central region of the endoscopic image acquired in the state shown in FIG. 6, as shown in FIG. 8.

Thus, when a lumen L is present at the central region of an endoscopic image, it means that the distal portion of the bending portion 12 is substantially straight, and that the flexible tube portion 13 continuous with the proximal side of the bending portion 12 is about to pass through the flexure 101, for example, located near the flexure 101. At this time, the bending stiffness of the flexible tube portion 13 should be changed.

Therefore, according to the present embodiment, the lumen detection section (cavity detection section) 33 detects whether or not a lumen L, which is a cavity, is in an approximately forward direction of the bending portion 12 (whether or not a cavity is present) on the basis of an image of the inside of the subject's body acquired by the endoscope apparatus 1 at the time of insertion. On the basis of the detection, the variable stiffness control section 36 transmits a variable stiffness section control signal for changing the bending stiffness of the flexible tube portion 13 to the variable stiffness sections 60. Hereinafter, the variable stiffness control of the flexible tube portion 13 according to the present embodiment will be described.

Figure 9:
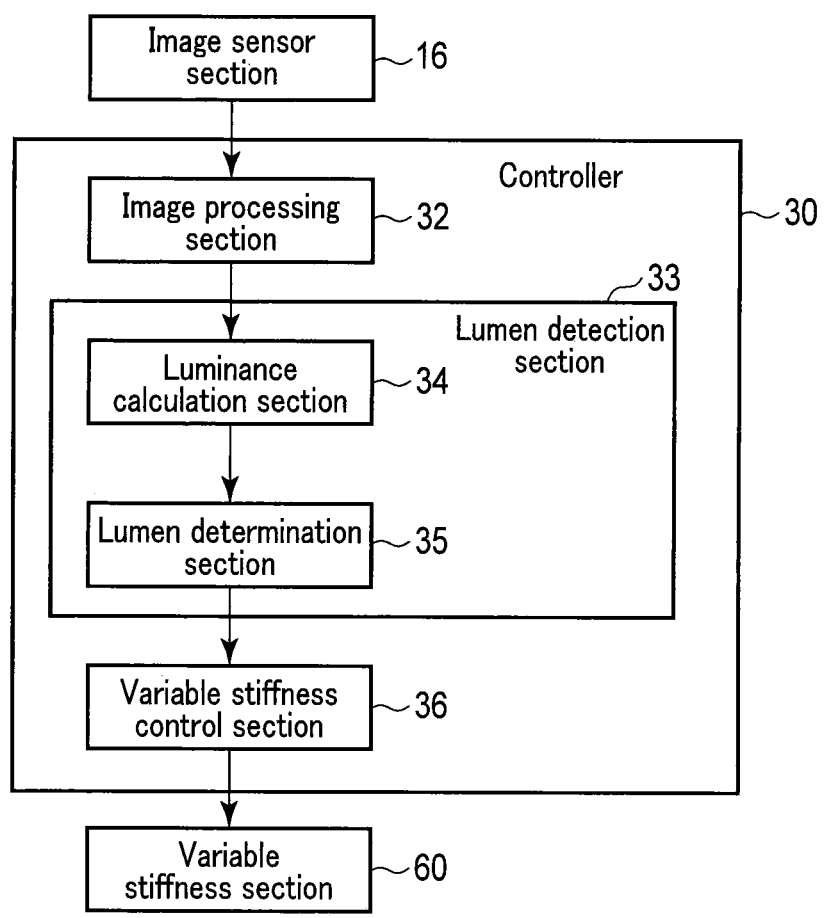
FIG. 9 is a block diagram illustrating variable stiffness control according to the first embodiment.

FIG. 9 is a block diagram illustrating variable stiffness control according to the first embodiment. FIG. 10 is a flowchart illustrating variable stiffness control according to the first embodiment. At step S11, the endoscope apparatus 1 images the inside of the intestinal tract using the image sensor section 16 during insertion into the large intestine. At next step S12, the image processing section 32 of the display control section 31 then performs image processing on the basis of an electric signal acquired by the image sensor section 16, and generates an endoscopic image inside of the intestinal tract 100. The generated image (image signal) is output to the luminance calculation section 34 of the lumen detection section 33, as shown in FIG. 9.

At step S13, the luminance calculation section 34 calculates a luminance value (brightness) from the output image signal. The luminance calculation section 34 calculates a luminance value at a central axis X on the screen image and a central axis Y on the screen image of the endoscopic image, as shown, for example, in FIGS. 11 and 12. A lumen detection area in the forward direction of the endoscopic image shown in FIGS. 11 and 12 will be referred to as D. The lumen detection area D is a predetermined area from the center of the endoscopic image, i.e. area at the center of the image, and is, for example, an area centered around the center of the image and defined by a circle having a predetermined radius. FIGS. 13 and 14 are graphs showing examples of a relationship between the central axis X on the screen image (pixel) and the luminance value in FIGS. 11 and 12, respectively.

Figure 11:
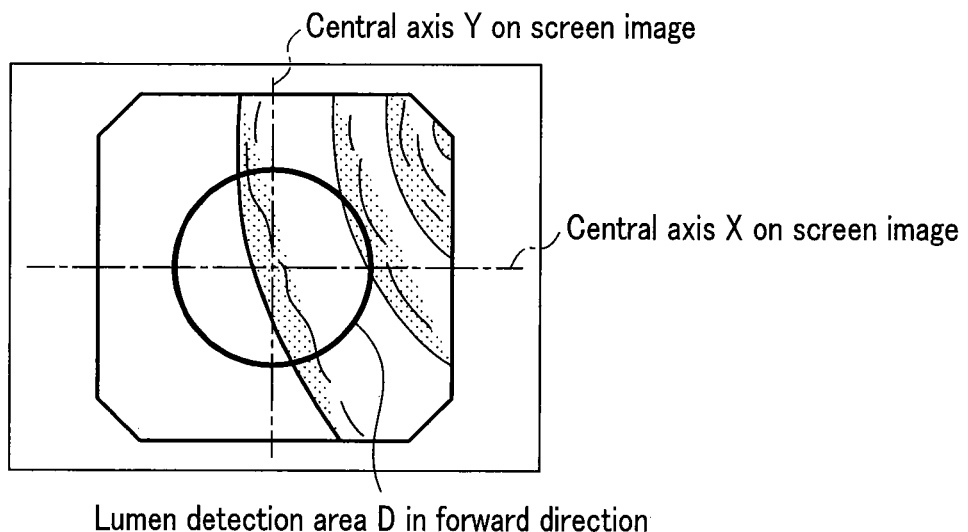
FIG. 11 shows an example of a lumen detection area in an endoscopic image shown in FIG. 7.
Figure 12:
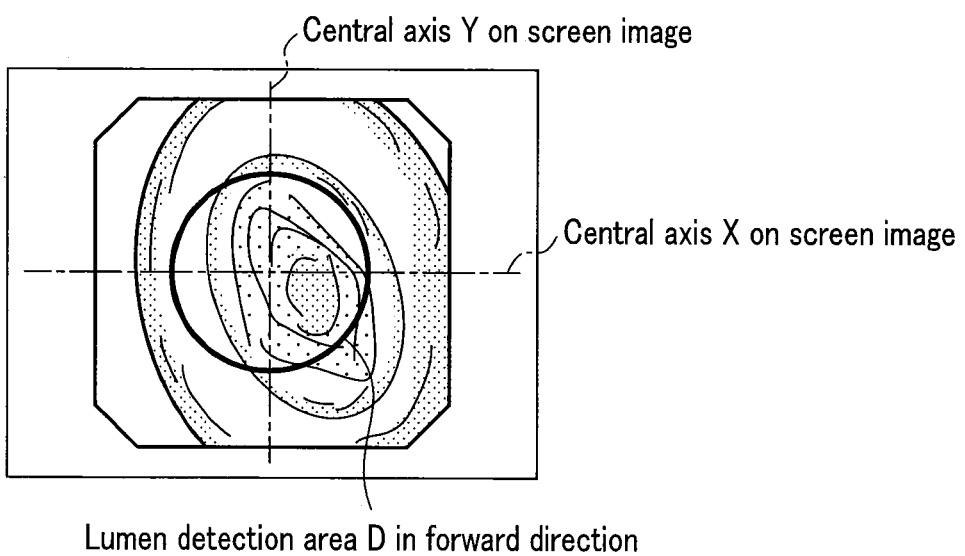
FIG. 12 shows an example of a lumen detection area in an endoscopic image shown in FIG. 8.

As shown in FIG. 11, when the distal face 19 of the bending portion 12 and the intestinal wall is close and the distal face 19 faces the intestinal wall, an endoscopic image of a bright intestinal wall is acquired. The luminance value of a pixel in the lumen detection area D calculated based thereon is relatively high (See FIG. 13). As shown in FIG. 12, when the distal face 19 and the intestinal wall are apart and the distal face 19 faces the lumen, an endoscopic image of a dark lumen leading to a deep portion of the intestinal tract is acquired. The luminance value of a pixel in the lumen detection area D calculated based thereon is relatively low (See FIG. 14).

At step S14, the lumen determination section 35 of the lumen detection section 33 determines whether or not a lumen L is in the forward direction of the distal face 19 of the bending portion 12, for example, whether or not the lumen L locates the lumen detection area D, on the basis of the luminance value calculated by the luminance calculation section 34. As shown in FIGS. 13 and 14, for example, using the greatest luminance value K1 outside the lumen detection area D and the average luminance value K2 in the lumen detection area D in regard to pixels on the central axis X on the screen image, the lumen determination section 35 determines whether or not the average luminance value K2 is less than half the maximum luminance value K1, namely, that K1/K2>2 is satisfied. Thus, the lumen determination section 35 determines, for example, whether or not the average luminance in the horizontal direction at the center of the lumen detection area D is less than ½ of the maximum luminance in the horizontal direction outside the lumen detection area.

If K1/K2>2 is satisfied (Yes), as shown in FIG. 14, the lumen determination section 35 determines that a lumen L is observed forward of the distal face 19, namely, a lumen L is present in the forward direction of the distal face 19. Accordingly, the processing goes to subsequent step S15, which is a variable stiffness control step.

If K1/K2≤2 is satisfied (No), as shown in FIG. 13, the lumen determination section 35 determines that a lumen L is not present in the forward direction of the distal face 19. Accordingly, the processing returns to step S11, where the image sensor section 16 images the inside of the intestinal tract 100 again.

The setting of the lumen detection area D, and the determination about whether or not a lumen L is present in the lumen detection area D on the basis of the luminance values K1 and K2, are not limited to those described above. The lumen determination section 35 may determine whether or not a lumen L is present using an average luminance value in the vertical direction (pixels on the central axis Y on the screen image) at the center of the lumen detection area D, or using only the luminance value in the lumen detection area D. For example, when the average luminance value K2 at the center of the lumen detection area D in the horizontal direction is less than a threshold value, the lumen determination section 35 determines that a lumen L is present in the forward direction of the distal face 19, and when the average luminance value K2 at the center of the lumen detection area D in the horizontal direction is equal to or greater than the threshold value, the lumen determination section 35 determines that a lumen L is not present in the forward direction of the distal face 19.

At step S15, the variable stiffness control section 36 transmits a variable stiffness section control signal to the variable stiffness section 60 to change the bending stiffness of the variable stiffness section 60 arranged in each segment of the flexible tube portion 13. Preferably, the segment including the variable stiffness section 60 whose bending stiffness is to be changed should be at least one segment including the segment next to the bending portion 12 among the flexible tube portion 13.

Figure 15:
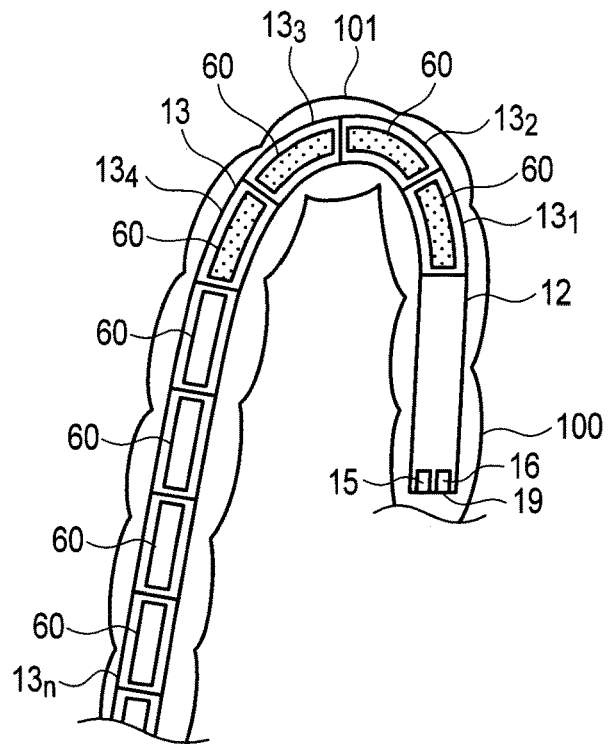
FIG. 15 is a diagram schematically showing an example of a state in which the bending portion is substantially straight along the intestinal tract and the flexible tube portion is bent along the intestinal tract while the insertion section is inserted into the large intestine in the first embodiment.

The variable stiffness control section 36 transmits, for example, a variable stiffness section control signal to the variable stiffness sections 60 to control the bending stiffness of each variable stiffness section 60, in such a manner that one or more variable stiffness sections 60 in the vicinity of the bending portion 12 or next to the bending portion 12 among the flexible tube portion 13 has a low bending stiffness value, that is, at least one segment corresponding to the at least one variable stiffness section 60 allows to be softened. In the example shown in FIG. 15, the variable stiffness control section 36 causes the variable stiffness sections 60 provided in the respective four segments in the flexible tube portion 13, namely, segment $13_1$ closest to the bending portion 12 to segment $13_4$, to have a low bending stiffness value. In FIG. 15, the variable stiffness sections 60 to be caused to be a low bending stiffness value are dotted. The number of segments whose bending stiffness is to be changed is not limited to the above-described number and may be conveniently set depending on the axial lengths of the segments and the variable stiffness sections 60, the general length of the flexure 101, and the like.

For example, when the bending stiffness of the entire flexible tube portion 13 is wholly high, the flexible tube portion 13 may not be properly bent in the flexure 101, causing extension of the intestinal wall at the flexure 101. This causes distress to the patient. Various approaches show that the force that bends the flexible tube portion 13 during insertion is reduced when the hand side (proximal side) of the flexible tube portion 13 is soft, and that the force is transmitted to the distal side more easily when the distal side has a bending stiffness higher than that of the proximal side. Accordingly, the variable stiffness control section 36 transmits, for example, a control signal for reducing the bending stiffness value of the flexible tube portion 13 in the vicinity of the flexure 101 (e.g., segments $13_1$ to $13_4$) to the corresponding variable stiffness section 60. This allows the segment of the flexible tube portion 13 in the vicinity of the flexure 101 to be soft and easily bent along the shape of the flexure 101. Since the segment located proximally on the flexible tube portion 13 is stiffer than the segment located distally on the flexible tube portion 13, the force pressing the insertion section 11 toward the direction of passage is easily transmitted.

Alternatively, the variable stiffness control section 36 may transmit a variable stiffness section control signal to the variable stiffness sections 60 to control the bending stiffness of each variable stiffness section 60, in such a manner that one or more variable stiffness sections 60 in the vicinity of the bending portion 12 or next to the bending portion has a high bending stiffness, that is, at least one segment corresponding to the at least one variable stiffness section 60 allows to be stiffened.

At step S16, the bending stiffness of each of the variable stiffness sections 60 is changed, and thereby the variable stiffness control ends up.

In the present embodiment, since a sensor that detects the bending shape of the flexible tube portion 13 is not arranged in the flexible tube portion 13, the bending shape itself of the flexible tube portion 13 during insertion cannot be determined. In the present embodiment, however, the lumen detection section 33 is provided to configure to detect a lumen L in the forward direction of the distal face 19 of the bending portion 12 on the basis of an image acquired by the imaging at the image sensor section 16 incorporated into the bending portion 12. It is thus possible to determine whether the bending portion 12 is located at the flexure 101 inside the intestinal tract 100 or located in a straight portion, on the basis of whether or not a lumen L is present in the forward direction of the distal face 19 detected by the lumen detection section 33.

On the basis of the result of detection of the lumen detection section 33, the variable stiffness control section 36 transmits a variable stiffness section control signal to the variable stiffness sections 60 to change the bending stiffness of the variable stiffness section 60 provided in each segment of the flexible tube portion 13. For example, when the lumen determination section 35 of the lumen detection section 33 determines that a lumen L is not present forward of the distal face 19 of the bending portion 12, it can be construed that the bending portion 12 is bent, and that the flexible tube portion 13 continuous with the bending portion 12 is substantially straight. Accordingly, the variable stiffness control section 36 does not transmit a variable stiffness section control signal. When the lumen determination section 35 determines that a lumen L is present forward of the distal face 19, it can be construed that the bending portion 12 is substantially straight, and that the flexible tube portion 13 continuous with the bending portion 12 is passing through the flexure 101 inside the intestinal tract 100. In such a case, the variable stiffness control section 36 transmits a variable stiffness section control signal and changes the bending stiffness of the variable stiffness section 60.

In the present embodiment, although the bending shape of the flexible tube portion 13 cannot be directly acquired, the bending state of the bending portion 12 provided immediately before the flexible tube portion 13 is determined on the basis of the endoscopic image acquired by the image sensor section 16 provided in the bending portion 12. Using the acquired bending state as a trigger, the lumen determination section 35 of the lumen detection section 33 determines that the flexible tube portion 13 is passing through the flexure 101, namely, that the bending stiffness of the flexible tube portion 13 should be changed.

The variable stiffness control section 36 controls the bending stiffness of each of the variable stiffness sections 60 in such a manner that the bending stiffness of the variable stiffness section 60 provided in at least one segment of the flexible tube portion 13 passing through the flexure 101 is changed, on the basis of the detection result of the lumen detection section 33. This allows, for example, the segment of the flexible tube portion 13 located in the vicinity of the flexure 101 to be easily bent along the shape of curvature of the flexure 101, thereby improving the ease of insertion.

In the present embodiment, since no sensor is provided in the flexible tube portion 13 to acquire its bending shape, the flexible tube portion 13 does not need to be increased in diameter. It is thus possible to provide a flexible tube insertion apparatus including the flexible tube portion 13 that has a small diameter and achieves an improved ease of insertion. In the present embodiment, not only in the flexible tube portion 13 but also in the bending portion 12 is provided no sensor which acquires its bending shape. It is thus possible to provide a flexible tube insertion apparatus including the bending portion 12 that has a small diameter and achieves an improved ease of insertion, without the need to increase the diameter of the bending portion 12.

According to the present embodiment, it is possible to provide a flexible tube insertion apparatus that changes the bending stiffness of the flexible tube portion 13 to follow the shape of curvature in the subject and thereby achieve an improved ease of insertion, by determining the bending state of the bending portion 12 on the basis of the endoscopic image acquired by the endoscope apparatus 1, thus determining the bending state of the flexible tube portion 13 based thereon, without providing a sensor in the flexible tube portion 13. It is also possible to provide a flexible tube insertion apparatus that reduces distress to the patient.

In the above description, a lumen L is detected in the forward direction of the bending portion 12 using an existing image sensor section 16 incorporated into the bending portion 12. However, a method of detecting a lumen (cavity) is not limited thereto, and any other detection method may be used. For example, an optical or ultrasonic distance sensor may be provided in the bending portion 12 and a distance between the distal face 19 of the bending portion 12 and the intestinal wall located forward of the distal face 19 may be calculated by the sensor. When the calculated distance is equal to or greater than a predetermined distance, the lumen determination section 35 determines that the distal face 19 faces a lumen L, namely, a lumen L is present in the forward direction. On the other hand, when the calculated distance is less than a predetermined distance, the distal face 19 faces the intestinal wall, namely, the lumen L is not present in the forward direction. On the basis of such determination, the lumen L can be detected.

In the present embodiment, a colonoscope is described by way of illustration, and a lumen in an intestinal tract is taken as an example of a cavity. The cavity is not limited to a lumen, and is, of course, applicable to various cavities.

[Variant]

Next, a variant of the first embodiment will be described.

As described above, the insertion section 11 is in a substantially straight state at first and passes through substantially straight area inside the intestinal tract 100. At this time, a lumen L is present in the central region of an endoscopic image acquired by the endoscope apparatus 1. As described with reference to FIGS. 5 to 8, even though a lumen L is not captured in the central region of the endoscopic image, there is a possibility that a lumen L is captured in the central region after that. It means that the distal portion of the bending portion 12 is substantially straight, and that the flexible tube portion 13 continuous with the proximal side of the bending portion 12 is about to pass through the flexure 101, for example, located near the flexure 101. At this time, namely, that the bending stiffness of the flexible tube portion 13 should be changed.

Thus, according to the present variant, after it is confirmed that a lumen L is in a substantially forward direction of the bending portion 12 on the basis of an image of the inside of the subject's body acquired by the endoscope apparatus 1 at the time of insertion and then the lumen detection section 33 detects that a lumen L is not in a substantially forward direction of the bending portion 12, the lumen detection section 33 detects that a lumen L is in the substantially forward direction of the bending portion 12, and the variable stiffness control section 36 transmits a variable stiffness section control signal to change the bending stiffness of the flexible tube portion 13 to the variable stiffness section 60 on the basis of the detection.

Figure 16:
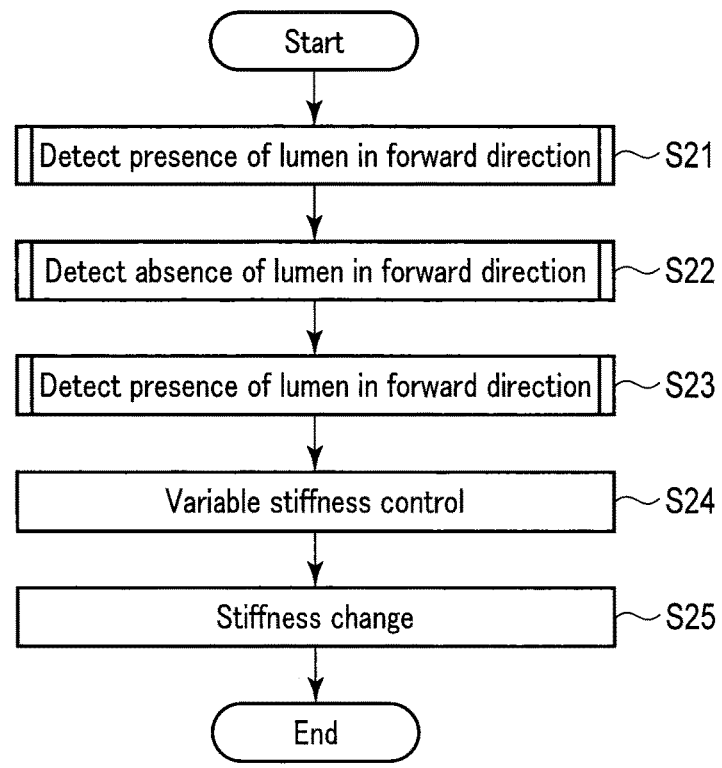
FIG. 16 is a flowchart illustrating variable stiffness control according to a variant.
Figure 17:
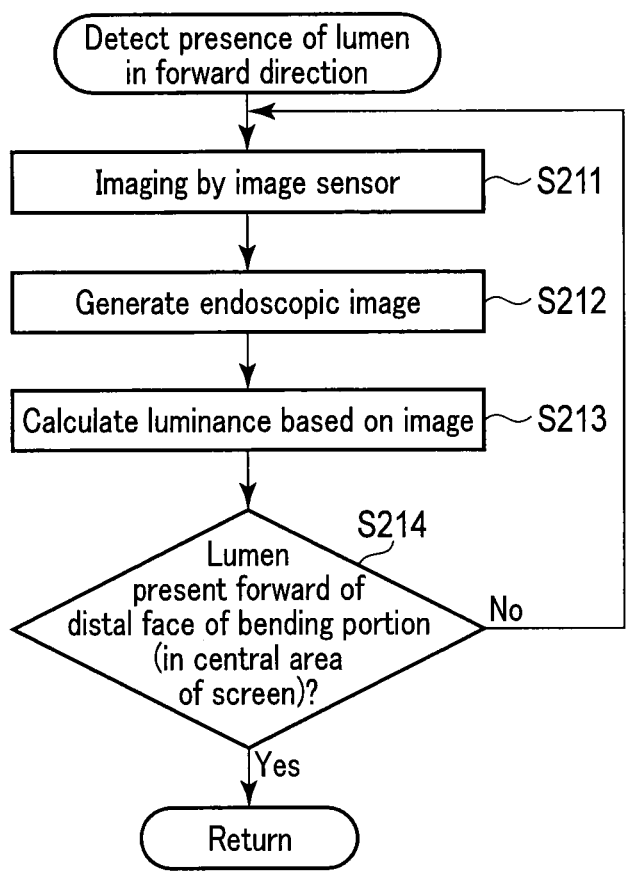
FIG. 17 is a flowchart for detecting that a lumen is present in a forward direction according to the variant.
Figure 18:
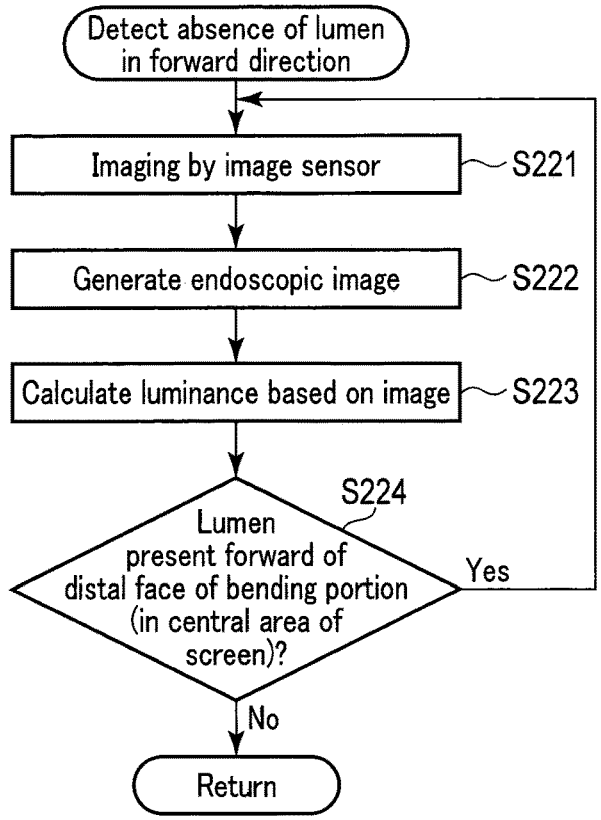
FIG. 18 is a flowchart for detecting that a lumen is not present in the forward direction according to the variant.

FIGS. 16-18 are flowcharts illustrating the variable stiffness control according to the variant. At step S21, the endoscope apparatus 1 detects that the lumen is present forward of the distal face 19 of the bending portion 12, for example, the lumen locates the central area of the screen image. Specifically, as shown in FIG. 17, the endoscope apparatus 1 images the inside of the intestinal tract using the image sensor section 16 during insertion into the large intestine at step S211. At next step S212, the image processing section 32 of the display control section 31 then performs image processing on the basis of an electric signal acquired at the image sensor section 16, and generates an endoscopic image inside of the intestinal tract 100. The generated image (image signal) is output to the luminance calculation section 34 of the lumen detection section 33. At step S213, the luminance calculation section 34 then calculates a luminance value from the output image signal. At step S214, the lumen determination section 35 of the lumen detection section 33 determines whether or not a lumen L is present forward of the distal face 19 of the bending portion 12, for example, whether or not the lumen L locates the lumen detection area D, on the basis of the calculated luminance value. When it is determined that a lumen L is not present (No), the processing returns to step S211, where the image sensor section 16 images the inside of the intestinal tract 100 again. When it is determined that a lumen L is present (Yes), the processing returns to the flow shown in FIG. 16, and goes to step S22.

At step S22, the endoscope apparatus 1 detects that the lumen is not present forward of the distal face 19 of the bending portion 12, for example, the lumen does not locate the central area of the screen image. Specifically, as shown in FIG. 18, the endoscope apparatus 1 performs imaging using the image sensor section 16, generates an endoscopic image using the image processing section 32 of the display control section 31, and calculates a luminance value using the luminance calculation section 34, at steps S221 to S223, in a manner similar to steps S211 to S213. At step S224, the lumen determination section 35 of the lumen detection section 33 determines whether or not a lumen L is present forward of the distal face 19 of the bending portion 12, for example, whether or not the lumen L locates the lumen detection area D, on the basis of the calculated luminance value. When it is determined that a lumen L is present (Yes), the processing returns to step S221, where the image sensor section 16 images the inside of the intestinal tract 100 again. When it is determined that a lumen L is not present (No), the processing returns to the flow of FIG. 16, and goes to step S23.

At step S23, the endoscope apparatus 1 detects that a lumen is present forward of the distal face 19 of the bending portion 12, for example, the lumen does not locate the central area of the screen image. Since step S23 is similar to step S21, a detailed description thereof will be omitted.

At step S24 after step S23, the variable stiffness control section 36 transmits a variable stiffness section control signal for changing the bending stiffness of the variable stiffness section 60 arranged in each segment of the flexible tube portion 13 to the variable stiffness sections 60. At next step S25, the bending stiffness of each of the variable stiffness sections 60 is changed, and thereby the variable stiffness control ends up.

According to the present variant, it is possible to suitably change the bending stiffness by determining the bending state of the bending portion 12, namely, whether or not the bending portion 12 locates at the flexure 101 inside the intestinal tract 100 or locates in a straight portion, more reliably than the first embodiment.

Alternatively, in another variant, a shape acquisition section may be provided to determine the bending state of the bending portion 12 on the basis of the amount of operation of the angle knob 17. The shape acquisition section may be a rotary encoder whose axis of rotation is attached to the axis of rotation of the angle knob 17. By combining the bending state acquired by the shape acquisition section and the lumen detection of the first embodiment, the bending state of the bending portion 12 can be determined more reliably, thus suitably changing the bending stiffness.

Hereinafter, the second to fourth embodiments of the present invention will be described. In the following, detailed explanations of the structures and operations similar to those in the first embodiment will be omitted, and only matters different from those of the first embodiment will be described.

Second Embodiment

The second embodiment of the present invention will be described with reference to FIG. 19.

Figure 19:
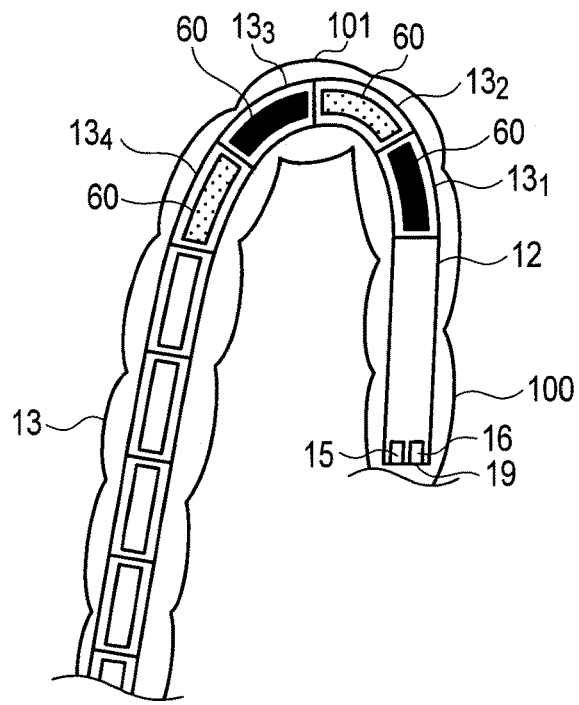
FIG. 19 is a diagram schematically showing an example of a state in which the bending portion is substantially straight along the intestinal tract and a flexible tube portion is bent along the intestinal tract while the insertion section is inserted into the large intestine in a second embodiment.

FIG. 19 is a diagram schematically showing an example of a state in which the insertion section 11 is inserted into the large intestine according to the second embodiment. FIG. 19 is a view substituting for FIG. 15 of the first embodiment.

Of the steps of the variable stiffness control flow shown in FIG. 10, only the specific control of the variable stiffness control at step S15 is different in the second embodiment from that of the first embodiment. In the second embodiment, at step 15, the variable stiffness control section 36 transmits a variable stiffness section control signal for controlling the bending stiffness of each variable stiffness section 60 to the variable stiffness sections 60 in such a manner that a variable stiffness section 60 with a low bending stiffness value and a variable stiffness section 60 with a high bending stiffness value are alternately arranged proximal to the flexible tube portion 13 along the axial direction of the insertion section 11 in the part of the flexible tube portion 13 in the vicinity of the bending portion 12 or next to the bending portion 12.

In the example shown in FIG. 19, the bending stiffness of the variable stiffness section 60 provided in each of four segments $13_1$ to $13_4$ is changed, in such a manner that the segment $13_1$ closest to the bending portion 12 in the flexible tube portion 13 allows to be stiffened (the corresponding variable stiffness section 60 has a high bending stiffness value), the segment $13_2$ adjacent thereto allows to be stiffened (the corresponding variable stiffness section 60 has a low bending stiffness value), the segment $13_3$ adjacent thereto is allowed to be stiffened, and the segment $13_4$ adjacent thereto allows to be softened. In FIG. 19, the variable stiffness sections 60 to be caused to be a high bending stiffness value are solidly shaded, and the variable stiffness sections 60 to be caused to be a low bending stiffness value are dotted. Thus, stiff segments and soft segments are alternately set in the flexible tube portion 13 located in the vicinity of the flexure 101. In the present embodiment, the number of segments whose bending stiffness is to be changed is not limited to the above-described number, and may be conveniently set.

In the example shown in FIG. 19, the bending stiffness value of the variable stiffness section 60 provided in the segment $13_1$ of the flexible tube portion 13 is set to be high, and the variable stiffness control section 36 controls the bending stiffness in such a manner that a stiff segment and a soft segment are alternately arranged. However, the control may be performed in such a manner that a soft segment and a stiff segment are alternately arranged by setting the bending stiffness value of the variable stiffness section 60 provided in the segment $13_1$ to be low.

According to the present embodiment, the variable stiffness control section 36 transmits a variable stiffness section control signal for controlling the bending stiffness of each variable stiffness section 60 to the variable stiffness sections 60 in such a manner that a plurality of segments of the flexible tube portion 13 are alternately set to soft and stiff states along the axial direction of the insertion section 11. By such variable stiffness control, it is possible to obtain a flexible tube insertion apparatus that ensures the ease of insertion appropriate for the bending state of the flexible tube portion 13 during insertion.

Third Embodiment

Figure 21:
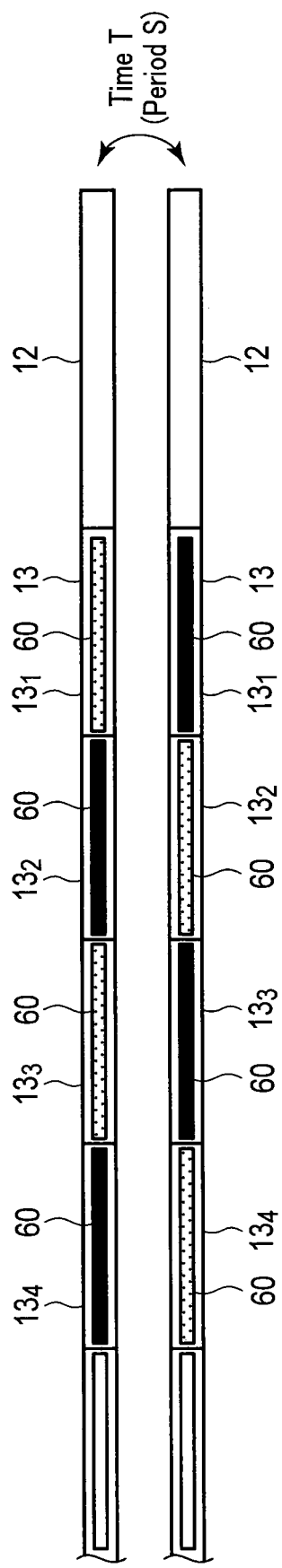
FIG. 21 is a diagram illustrating periodic switching of bending stiffness of variable stiffness sections according to the third embodiment.

The third embodiment of the present invention will be explained with reference to FIGS. 20 and 21.

FIG. 20 is a block diagram illustrating variable stiffness control according to the third embodiment. In the third embodiment, the controller 30 includes a time setting section 37, in addition to the display control section 31, the lumen detection section 33, and the variable stiffness control section 36. A time T at which the bending stiffness value of each of the variable stiffness sections 60 is changed, that is, period S at which switching is made between a stiff state and a soft state is input to the time setting section 37 from, for example, an input section not shown in the drawings. The time T may be conveniently set by the user, or may be set in advance in compliance with the endoscope 10 to be used.

Of the steps of the variable stiffness control flow shown in FIG. 10, only the specific control of the variable stiffness control at step S15 is different in the third embodiment from that of the first embodiment. In the third embodiment, the variable stiffness control section 36 reads a time T or period S set by the time setting section 37 at step S15. As in the second embodiment, the variable stiffness control section 36 transmits a variable stiffness section control signal for changing the bending stiffness of each variable stiffness section 60 to the variable stiffness sections 60 in such a manner that a variable stiffness section 60 with a low bending stiffness value and a variable stiffness section 60 with a high bending stiffness value are alternately arranged proximal to the flexible tube portion 13. Thereby, a soft segment $13_1$ and $13_3$ including a variable stiffness section 60 with a low bending stiffness value and a stiff segment $13_2$ and $13_4$ including a variable stiffness section 60 with a high bending stiffness value are alternately set in the flexible tube portion 13, as shown, for example, by the upper part of FIG. 21.

The variable stiffness control section 36 further transmits a variable stiffness section control signal for changing the bending stiffness of each variable stiffness section 60 to the variable stiffness sections 60 to periodically switch the relationship of levels between the bending stiffness values of adjacent variable stiffness sections 60 at a time T or period S. Thereby, a stiff segment $13_1$ and $13_3$ including a variable stiffness section 60 with a high bending stiffness value, and a soft segment $13_2$ and $13_4$ including a variable stiffness section 60 with a low bending stiffness value, are alternately set in the flexible tube portion 13 after the time T, as shown, for example, by the lower part of FIG. 21. Thus, the variable stiffness control section 36 automatically switches the relationship of levels between the bending stiffness of adjacent variable stiffness sections 60 each time T set by the time setting section 37.

As a matter of course, the original relationship between the bending stiffness value of the segments $13_1$ and $13_3$ and the bending stiffness value of the segments $13_2$ and $13_4$ of the flexible tube portion 13 may be opposite to the above-described relationship, and the number of segments whose bending stiffness is to be changed is not limited to the above-described number.

According to the present embodiment, a plurality of segments of the flexible tube portion 13 are alternately set to a stiff state and a soft state along the axial direction of the insertion section 11, and are automatically and periodically switched between the stiff and soft states at a preset time period. By performing such variable stiffness control, even if one of the segments of the flexible tube portion 13 has a bending stiffness that is not appropriate for passage through the flexure 101 at a certain timing, that segment will have a bending stiffness appropriate for passage through the flexure 101 at a timing when the bending stiffness is switched next. Such switching allows the user to advance the flexible tube portion 13, thus improving the ease of insertion.

Moreover, such periodic switching allows the force at the hand side to be easily transmitted to the distal end when the insertion section 11 is advanced. Furthermore, the distress on the large intestine is reduced, and the time required for insertion is reduced. Thus, according to the present embodiment, it is possible to provide a flexible tube insertion apparatus that conforms to complicated shapes of curvature inside of the intestinal tract and ensures the ease of insertion.

Fourth Embodiment

The fourth embodiment of the present invention will be described with reference to FIGS. 22 and 23.

Figure 22:
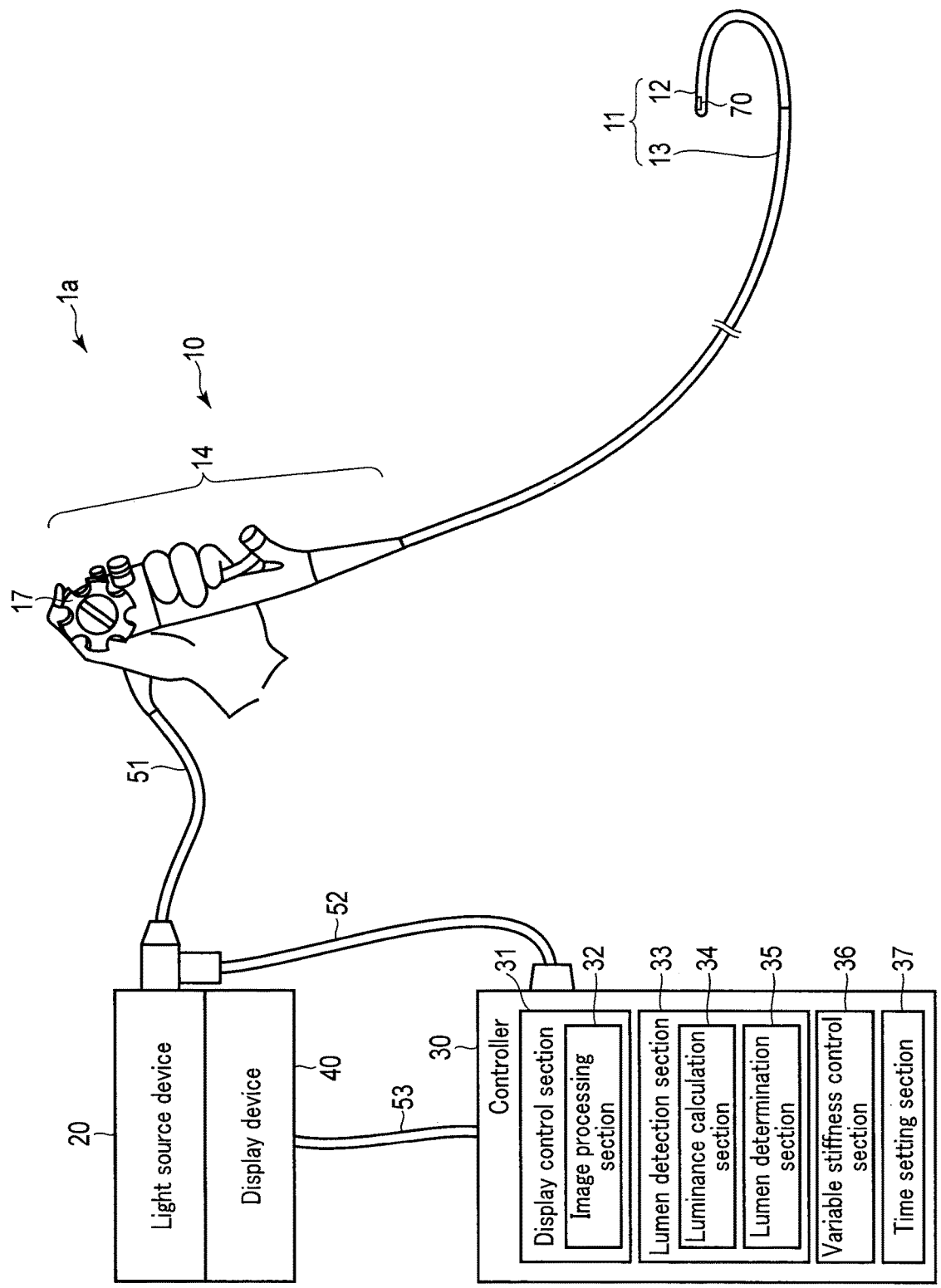
FIG. 22 is a diagram schematically showing a configuration of an endoscope apparatus according to a fourth embodiment.
Figure 23:
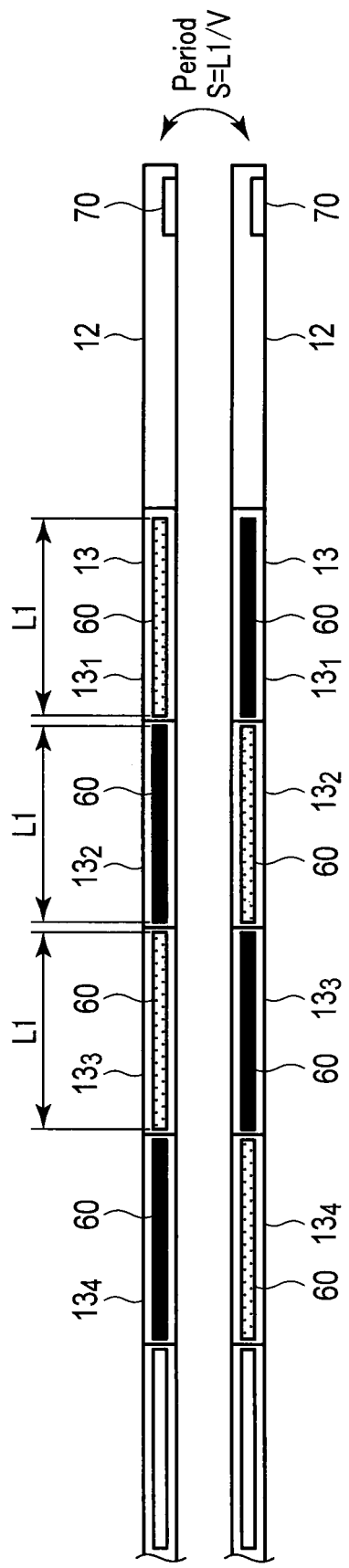
FIG. 23 is a diagram illustrating periodic switching of bending stiffness of variable stiffness sections according to the fourth embodiment.

FIG. 22 is a diagram schematically showing a configuration of an endoscope apparatus 1a according to the fourth embodiment. In the endoscope apparatus 1a, a distal speed detection section 70 is provided in the bending portion 12 located distally on the insertion section 11. The distal speed detection section 70 is, for example, a known acceleration sensor that detects the rate of change of speed with respect to time. The distal speed detection section 70 is incorporated, for example, into the distal portion of the bending portion 12.

The controller 30 includes the time setting section 37, as in the third embodiment. However, the time setting section 37 of the present embodiment is different from that of the third embodiment in that the time setting section 37 is connected to the distal speed detection section 70 via the cable 52 and the distal speed detection signal cable included in the universal cord 51. Speed information of the bending portion 12 detected by the distal speed detection section 70 is output to the time setting section 37. The time setting section 37 sets a time T at which the bending stiffness of each of the variable stiffness sections 60 is periodically changed, that is period S at which switching is made between stiff and soft states on the basis of the output speed information. In the present embodiment, the time T or period S is calculated by the time setting section 37 on the basis of the speed information of the bending portion 12 output from the distal speed detection section 70.

An example of the method of calculating the period S will be described. Let us assume that the longitudinal length of the variable stiffness section 60 in each segment of the flexible tube portion 13 is L1, as shown in FIG. 23. Assuming that the speed of the bending portion 12 detected by the distal speed detection section 70 is V, the time setting section 37 calculates and sets the period S as S=L1/V.

Of the steps of the variable stiffness control flow shown in FIG. 10, only the specific control of the variable stiffness control at step S15 is different in the fourth embodiment from that of the first embodiment, and the control is similar to that of the third embodiment. In the fourth embodiment, at step S15, the variable stiffness control section 36 reads the time T or period S set by the time setting section 37. The variable stiffness control section 36 transmits a variable stiffness section control signal for changing the bending stiffness of each variable stiffness section 60 to the variable stiffness sections 60 in such a manner that a variable stiffness section 60 with a low bending stiffness value and a variable stiffness section 60 with a high bending stiffness value are alternately arranged toward the proximal side of the flexible tube portion 13. Thereby, a soft segment $13_1$ and $13_3$ including a variable stiffness section 60 with a low bending stiffness value and a stiff segment $13_2$ and $13_4$ including a variable stiffness section 60 with a high bending stiffness value are alternately set in the flexible tube portion 13, as shown, for example, by the upper part of FIG. 23.

The variable stiffness control section 36 further transmits a variable stiffness section control signal for changing the bending stiffness of each variable stiffness section 60 to the variable stiffness sections 60 to periodically switch the relationship of levels between the bending stiffness values of adjacent variable stiffness sections 60 at a time T or period S calculated by the time setting section 37 on the basis of speed information from the distal speed detection section 70. Thereby, a stiff segment $13_1$ and $13_3$ including a variable stiffness section 60 with a high bending stiffness value, and a soft segment $13_2$ and $13_4$ including a variable stiffness section 60 with a low bending stiffness value, are alternately set in the flexible tube portion 13 after the time T, as shown, for example, by the lower part of FIG. 23.

In the present embodiment, the distal speed detection section 70 is provided in the bending portion 12, and the time setting section 37 calculates the period S at which the bending stiffness is changed, on the basis of the speed of the bending portion 12 detected by the distal speed detection section 70. By thus changing the bending stiffness of each of the variable stiffness sections 60 on the basis of the speed of the bending portion 12, the bending stiffness can be changed in accordance with the movement of the bending portion 12. It is thus possible to provide a flexible tube insertion apparatus with an improved ease of insertion.

The present invention has been described above based on the embodiments and the variants thereof, but the present invention is not limited to those embodiments. The present invention may be modified and changed in various manners, without departing from the spirit and scope of the invention. For example, the flexible tube insertion apparatus is not limited to the endoscope apparatus 1, and includes a wide range of insertion apparatuses comprising a flexible insertion section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   a tubular insertion section configured to be inserted into a subject, the insertion section including a bending portion located distally on the insertion section, the insertion section further including a flexible tube portion located proximal to the bending portion;
   a plurality of variable stiffness actuators, each provided in a corresponding one of a plurality of segments defined in a longitudinal axis direction of the flexible tube portion and configured to cause a change in a level of a bending stiffness of the flexible tube portion on a segment-by-segment basis;
   an image sensor provided in the bending portion and configured to image a forward direction of the bending portion; and
   a controller comprising hardware, the controller being configured to:
      control the change in the bending stiffness of the flexible tube portion by the variable stiffness actuators;
      detect a presence of a cavity in the forward direction of the bending portion, based on an image acquired by the image sensor;
      set a time period at which the bending stiffness is changed by the variable stiffness actuators, and
      control the changes in the bending stiffness of the variable stiffness actuators such that a relationship of levels between the bending stiffness of adjacent variable stiffness actuators is switched at the set time period when the presence of the cavity is detected in an approximately forward direction;
   wherein the controller controls the change in the bending stiffness of each of the variable stiffness actuators such that a variable stiffness actuator with a high bending stiffness value and a variable stiffness actuator with a lower variable stiffness value than the high bending stiffness value are alternately arranged proximal to the flexible tube portion along the longitudinal axis direction.

2. The flexible tube insertion apparatus according to claim 1, wherein the controller calculates a luminance of the image, and determines that the presence of the cavity is detected when an average luminance at a center of a cavity detection area of the image in a horizontal direction is less than ½ of a maximum luminance outside the cavity detection area in the horizontal direction.

3. The flexible tube insertion apparatus according to claim 1, wherein the controller calculates a luminance of the image, and determines that the presence of the cavity is detected when an average luminance at a center of a cavity detection area of the image in a horizontal direction is less than a threshold value.

4. The flexible tube insertion apparatus according to claim 1, wherein the bending portion comprises a distal speed detection sensor that detects a speed of the bending portion, and
   the controller sets the time period based on the speed detected by the distal speed detection sensor.

5. The flexible tube insertion apparatus according to claim 1, wherein the variable stiffness actuator comprises a variable stiffness material.

6. The flexible tube insertion apparatus according to claim 5, wherein the variable stiffness material comprises an electroactive polymer artificial muscle.

7. A method of operating a flexible tube insertion apparatus, the flexible tube insertion apparatus comprising:
   a tubular insertion section configured to be inserted into a subject, the insertion section including a bending portion located distally on the insertion section, the insertion section further including a flexible tube portion located proximal to the bending portion;
a plurality of variable stiffness actuators, each provided in a corresponding one of a plurality of segments defined in a longitudinal axis direction of the flexible tube portion and configured to cause a change in a level of a bending stiffness of the flexible tube portion on a segment-by-segment basis;
an image sensor provided in the bending portion and configured to image a forward direction of the bending portion; and
a controller comprising hardware, the controller being configured to:
control the change in the bending stiffness of the flexible tube portion by the variable stiffness actuators;
detect a presence of a cavity in the forward direction of the bending portion, based on an image acquired by the image sensor; and
set a time period at which the bending stiffness is changed by the variable stiffness actuators, the method comprising:
controlling the changes in the bending stiffness of the variable stiffness actuators by the controller such that a relationship of levels between the bending stiffness of adjacent variable stiffness actuators is switched at the set time period when the presence of the cavity is detected in an approximately forward direction;
wherein the controlling controls the change in the bending stiffness of each of the variable stiffness actuators such that a variable stiffness actuator with a high bending stiffness value and a variable stiffness actuator with a lower variable stiffness value than the high bending stiffness value are alternately arranged proximal to the flexible tube portion along the longitudinal axis direction.

* * * * *